United States Patent [19]
Hellstrand et al.

[11] Patent Number: 5,961,969
[45] Date of Patent: *Oct. 5, 1999

[54] STABLE CIRCULATING HISTAMINE LEVELS

[75] Inventors: Kristoffer Hellstrand, Göteborg; Svante Hermodsson, Mölndal, both of Sweden

[73] Assignee: Maxim Pharmaceuticals, Inc., San Diego, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/649,121

[22] Filed: May 14, 1996

[51] Int. Cl.$^6$ .................................................. A61K 45/05
[52] U.S. Cl. ...................... 424/85.1; 425/85.2; 425/85.7; 514/21; 530/321; 530/323; 530/324
[58] Field of Search .................................. 424/85.1, 85.2, 424/85.7; 514/21; 530/321, 323, 324

[56] References Cited

U.S. PATENT DOCUMENTS

| | | |
|---|---|---|
| 5,348,739 | 9/1994 | Hellstrand . |
| 5,478,211 | 12/1995 | Dominiak et al. ...................... 417/234 |

FOREIGN PATENT DOCUMENTS

| | | |
|---|---|---|
| 0 247 613 A2 | 12/1987 | European Pat. Off. . |
| 0 483 759 A1 | 10/1991 | European Pat. Off. ........ A61M 5/315 |
| 0 646 376 A1 | 5/1995 | European Pat. Off. ........ A61K 38/16 |
| 1 911 429 | 9/1970 | Germany . |
| 7-165582 | 6/1995 | Japan . |
| WO 91/04037 | 4/1991 | WIPO ............................ A61K 37/02 |
| WO 93/20803 | 10/1993 | WIPO .............................. A61K 9/20 |
| WO 93/24144 | 12/1993 | WIPO ............................ A61K 37/66 |
| WO 96/05289 | 2/1996 | WIPO .............................. C12N 5/08 |

OTHER PUBLICATIONS

Flavone–8–Acetic Acid Augments Systemic Natural Killer Cell Activity and Synergizes with IL–2 for Treatment of Murine Renal Cancer, Wiltrout, et al., *The Journal of Immunology*, 140(9):3261–3265, May 1, 1988.
Interleukin–2: Inception, Impact, and Implications, Smith, Kendall A., *Science*, 240:1169–1176, May 27, 1988.
Enhancement of Natural Killer Activity in Human Peripheral Blood by Flavone Acetic Acid, Urba, et al., *The Journal of the National Cancer Institute*, 80(7):521–525, Jun. 1, 1988.
The Development of New Immunotherapies for the Treatment of Cancer Using Interleukin–2, Rosenberg, *Annals of Surgery*, 208(2):121–135, Aug. 1988.
Interleukin 2 as a Pharmacologic Reagent, Lotze, eds., *National Institutes of Health*, Smith, Chapter 12, pp. 237–245, Oct. 28, 1988.
Augmentation of Natural Killer Activity, Induction of IFN and Development Tumor Immunity During the Successful Treatment of Established Murine Renal Cancer Using Flavone Acetic Acid and IL–2, Hornung, et al., *The Journal of Immunology*, 141(10):3671–3679, Nov. 15, 1988.

Enhancement of Human Natural Killer Cell Function by the Combined Effects of Tumor Necrosis Factor α or Interleukin–1 and Interferon–α or Interleukin–2, Østensen, et al., *Journal of Biological Response Modifiers*, 8:53–61, 1989.
Interleukin–2 can induce suppression of human natural killer cell cytotoxicity, Hellstrand, et al., *Clin. Exp. Immunol*, 77(3):410–416, 1989.
Biology of Natural Killer Cells Trinchieri, *Advances in Immunology*, 47:187–376, Accepted for Publication Jan. 23, 1989.
A Phase II Study of Interleukin–2 and Lymphokine–Activated Killer Cells in Patients with Metastatic Malignant Melanoma Dutcher, et al., *Journal of Clinical Oncology*, 7(4):477–485, Apr. 1989.
Comparative Effect of Recombinant IL–1, –2, –3, –4, and –6, IFN–γ, Granulocyte–Macrophage–Colony–Stimulating Factor, Tumor Necrosis Factor–α, and Histamine–Releasing Factors on the Secretion of Histamine From Basophils, Alam, et al., *The Journal of Immunology*, 142(10):3431–3435, May 18, 1989.
Activation of Natural Killer Cells via the p75 Interleukin 2 Receptor, Phillips, et al., *J. Exp. Med.*, 170:291–296, Jul. 1989.
Inhibition of Lymphokine–Activated Killer– and Natural Killer–Mediated Cytotoxicities by Neutrophils, Shau, et al., *The Journal of Immunology*, 143(3):1066–1072, Aug. 1989.
Regulation of Human Basophil Mediator Release by Cytokines, Schleimer, et al., *The Journal of Immunology*, 143(4):1310–1317, Aug. 15, 1989.
Inhibition of Lymphokine–activated Killer Cell Function by Human Alveolar Macrophages, Roth, et al., *Cancer Research*, 49:4690–4695, Sep. 1989.
A Cell–to–Cell Mediated Interaction Involving Monocytes and Non$^-$T/CD16$^+$ Natural Killer (NK) Cells is Required for Histamine H$_2$–Receptor–Mediated NK–Cell Activation, Hellstrand, et al., *Scand J. Immunol*, 31:631–644, 1990.
Deficiency in Catalase Activity Correlates with the Appearance of Tumor Phenotype in Human Keratinocytes, Rabilloud, et al., *Int. J. Cancer*, 45:952–956, 1990.
Enhancement of Human Natural Killer Cell Cytotoxicity by Serotonin: Role of Non–T/CD16$^+$ NK Cells, Accessory Monocytes, and 5–HT$_{1A}$ Receptors, Hellstrand, et al., *Cellular Immunology*, 127:199–214, 1990.

(List continued on next page.)

Primary Examiner—Cecilia J. Tsang
Assistant Examiner—Patrick R. Delaney
Attorney, Agent, or Firm—Knobbe, Martens, Olson & Bear, LLP

[57] ABSTRACT

Methods for obtaining beneficial stable levels of circulating histamine are disclosed for use in methods for enhancing natural killer cell cytotoxicity. In such methods, a beneficial level of circulating histamine is attained and an agent whose ability to enhance natural killer cell cytotoxicity is augmented by histamine is administered. Alternatively, stable beneficial levels of circulating histamine can be attained in subjects receiving chemotherapy or antiviral treatment. The invention may also be employed in treatments combining histamine, agents which enhance natural killer cell cytotoxicity, and chemotherapeutic agents.

37 Claims, 1 Drawing Sheet

OTHER PUBLICATIONS

Flavone acetic acid antitumour activity against a mouse pancreatic adenocarcinoma is mediated by natural killer cells, Damia, et al., *Cancer Immunol Immunother*, 32:241–244, 1990.

Monocyte–Mediated Suppression of IL–2–Induced NK–Cell Activation, Hellstrand, et al., *Scand J. Immunol*, 32(2):183–192, 1990.

Possible involvement of adenosine 3':5'–cyclic monophosphate and extracellular calcium ions in histamine stimulation of interleukin–1 release from macrophage–like P388D1 cells, Okamoto, et al., *Immunology*, 70:186–190, 1990.

Synergistic Activation of Human Natural Killer Cell Cytotoxicity by Histamine and Interleukin–2, Hellstrand, et al., *Int. Arch. Allergy Appl. Immunology*, 92:379–389, 1990.

Histamine Type 2–Receptor Antagonists and Cancer Immunotherapy, Tom Smith, MD, *Comprehensive Therapy*, 16(1):8–13, 1990.

Splenic Versus Hepatic Artery Infusion of Interleukin–2 in Patients with Liver Metastases, Mavligit, et al., *Journal of Clinical Oncology*, 8(2):319–324, 1990.

Renal Cell Carcinoma: Treatment With Recombinant Interleukin–2 Plus Beta–Interferon, Krigel, et al., *Journal of Clinical Oncology*, 8(3):460–467, Mar. 1990.

High–Dose Recombinant Interleukin–2 Alone: A Regimen With Limited Activity in the Treatment of Advanced Renal Cell Carcinoma, Abrams, et al., *Journal of the National Cancer Institute*, 82(14):1202–1206, Jul. 18, 1990.

Recombinant Interleukin–2 and Adoptive Immunotherapy Alternated with Dacarbazine Therapy in Melanoma: A National Biotherapy Study Group Trial, Dilman, et al., *Journal of the National Cancer Institute*, 82(16):1345–1348, Aug. 15, 1990.

Immunological Effects of Flavone Acetic Acid, Triozzi, et al., *Cancer Research*, 50:6483–6485, Oct. 15, 1990.

Role of Histamine in Natural Killer Cell–Mediated Resistance Against Tumor Cells, Hellstrand, et al., *The Journal of Immunology*, 145(12):4366–4370, Dec. 15, 1990.

Treatment of acute myeloid leukaemia patients with recombinant interleukin 2: a pilot study Foa, et al., *British Journal of Haematology*, 77:491–496, 1991.

Cell–to–Cell Mediated Inhibition of Natural Killer Cell Proliferation by Monocytes and its Regulation by Histamine $H_2$–Receptors, Hellstrand, et al., *Scand J. Immunol*, 34:741–752, 1991.

Induction of Natural Killer Activity by Xanthenone Analogues of Flavone Acetic Acid: Relation with Antitumour Activity, Ching, et al., *Eur. J. Cancer*, 27(1):79–83, 1991.

In vitro Methods for Screening Agents with an Indirect Mechanism of Antitumour Activity: Xanthenone Analogues of Flavone Acetic Acid, Ching, et al., *Eur. J. Cancer*, 27(12):1684–1689, 1991.

Monocyte–Induced Down–Modulation of CD16 and CD56 Antigens on Human Natural Killer Cells and its Regulation by Histamine $H_2$–Receptors, Hellstrand, et al., *Cellular Immunology*, 138:44–45, 1991.

Natural killer (NK) and lymphokine activated killer (LAK) cell activity in patients (PTS) treated with Flavone acetic acid (FAA), Galligioni, *Annals of Oncology*, 2:145–150, 1991.

Production of Large Amounts of Hydrogen Peroxide by Human Tumor Cells, Szatrowski, et al., *Cancer Research*, 51:794–798, Feb. 1991.

A Phase II Study of High–Dose Continuous Infusion Interleukin–2 With Lymphokine–Activated Killer Cells in Patients With Metastatic Melanoma, Dutcher, et al., *Journal of Clinical Oncology*, 9(4):641–648, Apr. 1991.

Continuous Interleukin–2 and Lymphokine–Activated Killer Cells for Advanced Cancer: A National Biotherapy Study Group Trial, Dillman, et al., *Journal of Clinical Oncology*, 9(7):1233–1240, Jul. 1991.

Sequential Administration of Recombinant Human Interleukin–2 and Dacarbazine in Metastatic Melanoma: A Multicenter Phase II Study, Stoter, et al., *Journal of Clinical Oncology*, 9(9):1687–1691, Sep. 1991.

Interactions between human monocytes and tumor cells. Monocytes can either enhance or inhibit the growth and survival of K562 Cells, Davies, et al., Nov. 1991.

Effects of Flavonoids on Immune and Inflammatory Cell Functions, Middleton, et al., *Biochemical Pharmacology*, 43(6):1167–1179, 1992.

Immunotherapy of mammary adenocarcinoma metastases in C3H/HeN mice with chronic administration of cyclo–oxygenase inhibitors alone or in combination with IL–2 Khoo, et al., *Clin. Exp. Metastasis*, 10(4):239–252, 1992.

Oxygen Free Radical Generation and Regulation of Proliferative Activity of Human Mononuclear Cells Responding to Different Mitogens, Whitacre, et al., *Cellular Immunology*, 144:287–295, 1992.

A phase II study of interleukin–2 and interferon–alpha in head and neck cancer, Schantz, et al., *Investigational New Drugs*, 10:217–223, 1992.

Regulation of the Natural Killer Cell Response to Interferon–$\alpha$ by Biogenic Amines, Hellstrand, et al., *Journal of Interferon Research*, 12:199–206, 1992.

A Randomized Phase II Trial of Continuous Infusion Interleukin–2 or Bolus Injection Interleukin–2 Plus Lymphokine–Activated Killer Cells for Advanced Renal Cell Carcinoma, Weiss, et al., *Journal of Clinical Oncology*, 10(2):275–281, Feb. 1992.

Natural Killer (NK) Cell Stimulatory Factor Increases the Cytotoxic Activity of NK Cells from Both Healthy Donors and Human Immunodeficiency Virus–infected Patients, Chehimi, et al., *Journal of Experimental Medicine*, 175:789–796, Mar. 1992.

Chemoimmunotherapy of Metastatic Murine Renal Cell Carcinoma Using Flavone Acetic Acid and Interleukin 2, Salup, et al., *The Journal of Urology*, 147:1120–1123, Apr. 1992.

Phase I Trial of High–Dose Bolus Interleukin–2 and Interferon Alfa–2a in Patients With Metastatic Malignancy, Budd, et al., *Journal of Clinical Oncology*, 10(5):804–809, May 1992.

Prolonged Continuous Intravenous Infusion Interleukin–2 and Lymphokine–Activated Killer–Cell Therapy for Metastatic Renal Cell Carcinoma, Thompson, et al., *Journal of Clinical Oncology*, 10(6):960–968, Jun. 1992.

Phase II Study of Subcutaneous Interleukin–2 in Unselected Patients With Advanced Renal Cell Cancer on an Outpatient Basis, Sleijfer, et al., *Journal of Clinical Oncology*, 10(7):1119–1123, Jul. 1992.

A Phase II Trial of Interleukin–2 and Interferon Alfa–2a in Patients With Advanced Renal Cell Carcinoma, Ilson, et al., *Journal of Clinical Oncology*, 10(7):1124–1130, Jul. 1992.

Effect of indomethacin plus ranitidine in advanced melanoma patients on high–dose interleukin–2 Mertens, et al., *The Lancet*, 340:397–398, Aug. 15, 1992.

Effects of Cancer Immunotherapy with Indomethacin and Interleukin–2 on Murine Hemopoietic Stem Cells, Saarloos, et al., *Cancer Research,* 52:6452–6462, Dec. 1, 1992.

Effects of histamine type–2 receptor antagonists on indomethacin and IL–2 immunotherapy of metastasis, Saarloos, et al., *Clin. Exp. Metastasis,* 11(3):275–283, 1993.

Serotonergic 5–HT$_{1A}$ Receptors Regulate a Cell Contact––Mediated Interaction between Natural Killer Cells and Monocytes, Hellstrand, et al., *Scand J. Immunol.* 37:7–18, 1993.

Sustained Indomethacin and Ranitidine with Intermittent Continuous Infusion Interleukin–2 in Advanced Malignant Melanoma: A Phase II Study, Mertens, et al., *Clinical Oncology,* 5(2):107–113, 1993.

Selective Modulation of Human Natural Killer Cells In Vivo After Prolonged Infusion of Low Dose Recombinant Interleukin 2 Caligiuri, et al., *J. Clin. Invest.,* 91:123–132, Jan. 1993.

Effect of Reactive Oxygen Intermediates and Antioxidants on Proliferation and Function of T Lymphocytes Dröge, et al., *Methods in Enzymology,* 234:135–151, 1994.

Histamine in immunotherapy of advanced melanoma: a pilot study Hellstrand, et al., *Cancer Immunol Immunother.* 39:416–419, 1994.

Histaminergic regulation of antibody–dependent cellular cytotoxicity of granulocytes, monocytes, and natural killer cells Hellstrand, et al., *Journal of Leukocyte Biology,* 55:392–397, Mar. 1994.

Phase II Study of Subcutaneous rHu Interleukin–2 in Patients with Acute Myelogenous Leukemia in Partial or Complete Second Remission and Partial Relapse Shepherd, et al., *British Journal of Haematology,* Supp. 1, 87:205, Jun. 1994.

Hydrogen peroxide as a potent activator of T lymphocyte functions Los, et al., *Eur. Journal of Immunology,* 25:159–165, 1995.

Histaminergic Regulation of NK Cells Hellstrand, et al., *Journal of Immunology,* 153(11):4940–4947, Dec. 1, 1994.

Remission maintenance therapy with histamine and interleukin–2 in acute myelogenous leukaemia Brune, et al., *British Journal of Haematlogy,* 92:620–626, 1996.

Induction of lymphokine activated killer cells in serum–free medium Froelich, et al., *Journal of Immunological Methods,* 86(2):205–211, (1986).

Peptide derivative cytochrome inhibit enzyme system oxidation burst phagocyte cell inflammation disease Malech, et al., Database WPI/Derwent (Abstract), Jul. 25, 1989.

Effects of Histamine on IgG3 Monoclonal Antibody Directed Effector Cell Lysis of Tumor Cells Welt, et al., *Proceedings of ASCO,* 7:164, Abstract 632, Mar. 1988.

Role of Histamine in Natural Killer Cell–Dependent Protection Against Herpes Simplex Virus Type 2 Infection Hellstrand, et al., *Clinical and Diagnostic in Mice Laboratory Immunology,* 2(3):277–280, May 1995.

Database WPI, Section Ch, Week 9534, Derwent Publications Ltd., London, GB; Class B04, AN 95–261204, XP002036365 and JP 07 165 582 A (Takayama, S.) abstract (1995).

The Influence of Intraperitoneal Injections of Histamine on Tumour Growth in Fibrosarcoma–Bearing Mice, Burtin, et al., *Cancer Letters,* 12(3):195–201, Jan. 1981.

Successful Tumour Immunotherapy with Cimetidine in Mice, Osband, et al., *The Lancet,* No. 8221, 1:636–638, Mar. 21, 1981.

Factors Regulating Availability of Histamine at Tissue Receptors Ganellin and Parsons, eds., *Pharmacology of Histamine Receptors,* Beaven, Chapter Three, pp. 103–145, © 1982.

Hydroxyl radical scavengers inhibit lymphocyte mitogenesis Novogrodsky, et al., *Proc. Natl. Acad. Sci. USA,* 79:1171–1174, Feb. 1982.

Suppression of Natural Killing in Vitro by Monocytes and Polymorphonuclear Leukocytes, Seaman, et al., *The Journal of Clinical Investigation,* 69:876–888, Apr. 1982.

The Differential Effects of Human Leukocytic Pyrogen/Lymphocyte–Activating Factor, T Cell Growth Factor, and Interferon on Human Natural Killer Activity, Dempsey, et al., *The Journal of Immunology,* May 17, 1982.

Tumor–Enhancing Effects of Cimetidine, Barna, et al., *Oncology,* 40:43–45, 1983.

Decreased blood histamine levels in patients with solid malignant tumors Burtin, et al., *Br. J. Cancer,* 47:367–372, 1983.

Combination of Cimetidine with other Drugs for Treatment of Cancer, Thornes, et al., *New England Journal of Medicine* 308:591–592, Mar. 10, 1983.

The Effect of Histamine, Antihistamines, and a Mast Cell Stabilizer on the Growth of Cloudman Melanoma Cells in DBA/2 Mice Nordlund, et al., *Journal of Investivative Dermatology,* 81(1):28–31, Jul. 1983.

The Influence of Histamine on Immune and Inflammatory Responses, Beer, et al., *Advances in Immunology,* 35:209–268, 1984.

Hydroxyl radical scavengers inhibit human natural killer cell activity, Suthanthiran, et al., *Nature* 307:276–278, Jan. 1984.

Enhancement by serotonin of intra–tumour penetration of spleen cells, Lespinatas, et al., *Br. J. Cancer,* 50:545–547, Apr. 5, 1984.

Compared Mechanisms of Tumor Cytolysis by Human Natural Killer Cells and Activated Polymorphonuclear Leukocytes, Abrams, et al., *The Journal of Immunology* 132(6):3192–3196, Jun. 1984.

Down–Regulation of Human Natural Killer Activity Against Tumors by the Neutrophil Myeloperoxidase System and Hydrogen Peroxide, El–Hag, et al., *The Journal of Immunology* 133(6):3291–3297, Dec. 1984.

Effect of Ascorbic Acid on Human Natural Killer Cells, Huwyler, et al., *Immunology Letters,* 10:173–176, 1985.

The Role of Natural Killer Cells in the Control of Tumor Growth and Metastasis, Nabil Hanna, *Biochimica et Biophysica Acta,* 780:213–226, 1985.

Induction of Interferon–γ Production by Human Natural Killer Cells Stimulated by Hydrogen Peroxide, Munakata, et al., *The Journal of Immunology,* 134(4):2449–2455, Apr. 1985.

Natural Killer Cell–Mediated Lysis Involves an Hydroxyl Radical–Dependent Step, Duwe, et al., *The Journal of Immunology,* 134(4):2637–2644, Apr. 1985.

Cytotoxicity by human adherent cells: oxygen–dependent and –independent cytotoxic reactions by different cell populations, Kessel, et al., *Immunology,* 58:291–296, 1986.

Histamine augments interleukin–2 production and the activation of cytotoxic T lymphocytes, Droege, et al., *Chemical Abstracts,* 104:No. 146898m, p. 146891, 1986.

Histamine Augments Interleukin–2 Production and the Activation of Cytotoxic T Lymphocytes, Dröge, et al., *Immunopharmacology,* 11:1–6, 1986.

Histamine Inhibits Interferon–γ Production via Suppression of Interleukin 2 Synthesis, Dohlsten, et al., *Cellular Immunology*, 101:493–501, 1986.

Histamine–Induced Suppressor Factor Inhibition of NK Cells: Reversal with Interferon and Interleukin 2, Nair, et al., *The Journal of Immunology*, 136(7):2456–2462, Apr. 1, 1986.

Hydeoperoxide Metabolism in Cyanobacteria, Tel–Or, et al., *Archives of Biochemistry and Biophysics*, 246(1):396–402, Apr. 1986.

Histamine $H_2$–Receptor–Mediated Regulation of Human Natural Killer Cell Activity, Hellstrand, et al., *The Journal of Immunology*, 137(2):656–660, Jul. 15, 1986.

Biogenic Amines in the Regulation of Human Natural Killer Cell Cytotoxicity (Thesis), Hellstrand, *Medi Press, Göteborg, Sweden*, 1987.

Differential Effects of Histamine Receptor Antagonists on Human Killer Cell Activity, Hellstrand, et al., *Int. Archs Allergy appl. Immunology*, 84:247–255, 1987.

Selective, Histamine–Mediated Immunosuppression in Laryngeal Cancer, Richtsmeier, et al., *Ann Otol Rhinol Laryngol*, 96(5):569–572, 1987.

Thyroid Hermone Regulates TRH Biosysnthesis in the Paraventricular Necleus of the Rat Hypothalamus Segerson, et al., *Science*, 238:78–80 1990.

A Progress Report on the Treatment of 157 Patients With Advanced Cancer Using Lymphokine–Activated Killer Cells and Interleukin–2 or High–Dose Interleukin–2 Alone Rosenberg, et al., *N. Eng. Journal of Medicine*, 316(15):889–897, Apr. 9, 1987.

Clinical Improvement in Advanced Cancer Disease After Treatment Combining Histamine and H2–Antihistaminics (Ranitidine or Cimetidine) Burtin, et al., *Eur. Journal of Cancer Clin. Oncol.*, 24(2):161–167, 1988 (Accepted Jun. 1987).

Identification of Cellular Mechanisms Operational In Vivo During the Regression of Established Pulomonary Metastases by the Systemic Administration of High–Dose Recombinant Interleukin 2 Mulé, et al., *Journal of Immunology*, 139(1):285–294, Jul. 1987.

Role of Serotonin in the Regulation of Human Natural Killer Cell Cytotoxicity, Hellstrand, et al., *The Journal of Immunology*, 139(2):869–875, Aug. 1, 1987.

The IL–2 Receptor β Chain (p70): Role in Mediating Signals for LAK, NK, and Proliferative Activities, Siegel, et al., *Science*, vol. 238, Oct. 2, 1987.

Chondrocyte Antioxidant Defenses: The Roles of Catalase and Glutathione Peroxidase in Protection Against $H_2O_2$ Dependent Inhibition of Proteoglycan Biosynthesis, Baker, et al., *The Journal of Rheumatology*, 15(4):670–677, 1988.

Clinical Improvement in Advanced Cancer Disease After Treatement Combining Histamine and H2–Antihistaminics (Ranitidine or Cimetidine) Burtin, et al.,*Eur. J. Clin. Oncol.*, 24(2):161–167, 1988.

Antioxidants Inhibit Proliferation and Cell Surface Expression of Receptors for Interleukin–2 and Transferrin in T Lymphocytes Stimulated with Phorbol Myristate Acetate and Ionomycin Chaudhri, et al., *Cellular Immunology*, 115:204–213, 1988.

Role of Flavonoids in the Oxygen–Free Radical Modulation of the Immune Response, Pignol, et al., *Plant Flavonoids in Biology & Medicine II: Biochemical, Cellular . . .*, 173–182, 1988.

STABLE CIRCULATING HISTAMINE LEVELS

BACKGROUND OF THE INVENTION

The present invention relates to methods of treating cancer or infectious disease in which histamine is administered in conjunction with additional agents. The additional agent may be an agent which stimulates the cytotoxic activity of natural killer cells in a synergistic fashion with histamine. Alternatively, the additional agent may be a chemotherapeutic, antiviral, or antibiotic agent. Methods combining histamine, agents which act synergistically with histamine to increase NK cell cytotoxicity, and chemotherapeutic agents are also contemplated.

The invention is based on the surprising observation that despite previous reports of histamine's short half life in the body, it is possible to attain stable beneficial levels of circulating blood histamine and to maintain these beneficial levels for hours or days after the last administration of histamine. This observation facilitates treatments in which histamine administration to obtain beneficial levels of circulating blood histamine is combined with treatment with other agents. A brief review of the observations leading to the present invention is provided below to place the present invention in context.

A. Cell Types Involved in the Generation of an Immune Response

Recent anticancer strategies have focussed on utilizing the host immune system as a means of cancer treatment or therapy. The immune system has evolved complex mechanisms for recognizing and destroying foreign cells or organisms present in the body of the host. Harnessing the body's immune mechanisms is an attractive approach to achieving effective treatment of malignancies.

A wide array of effector cells, each having its own characteristics and role, implement the immune response. One type of effector cell, the B cell, generates antibodies targeted against foreign antigens encountered by the host. In combination with the complement system, antibodies direct the destruction of cells or organisms bearing the targeted antigen.

Another type of effector cell, the T cell, is divided into subcategories which play different roles in the immune response. Helper T cells secrete cytokines which stimulate the proliferation of other cells necessary for mounting an effective immune response, while suppressor T cells down regulate the immune response. A third category of T cell, the cytotoxic T cell, is capable of directly lysing a targeted cell presenting a foreign antigen on its surface.

An additional type of effector cell is the natural killer cell (NK cell), a type of lymphocyte having the capacity to spontaneously recognize and destroy a variety of malignant cell types. This characteristic of NK cells makes them an attractive candidate for exploitation in cancer treatments and therapies based on using the host's immune system as a weapon against malignant tumors.

B. Cytokines Involved Mediating the Immune Response

The interplay between the various effector cells listed above is influenced by the activities of a wide variety of chemical factors which serve to enhance or reduce the immune response as needed. Such chemical modulators may be produced by the effector cells themselves and may influence the activity of immune cells of the same or different type as the factor producing cell.

One category of chemical mediators of the immune response is cytokines, molecules which stimulate a proliferative response in the cellular components of the immune system.

Interleukin-2 (IL-2) is a cytokine synthesized by T cells which was first identified in conjunction with its role in the expansion of T cells in response to an antigen (Smith, K. A. Science 240:1169 (1988). Several studies have demonstrated that IL-2 has antitumor effects that make it an attractive agent for treating malignancies (see e.g. Lotze, M. T. et al, in "Interleukin 2", ed. K. A. Smith, Academic Press, Inc., San Diego, Calif., p237 (1988); Rosenberg, S., Ann. Surgery 208:121 (1988)). In fact, IL-2 has been utilized to treat subjects suffering from malignant melanoma, renal cell carcinoma, and acute myelogenous leukemia. (Rosenberg, S. A. et al., N. Eng. J. Med. 316:889–897 (1978); Bukowski, R. M. et al., J. Clin. Oncol 7:477–485 (1989); Foa, R. et al., Br. J. Haematol. 77:491–496 (1990)).

It appears likely that NK cells are responsible for the anti-tumor effects of IL-2. For example, IL-2 rapidly and effectively augments the cytotoxicity of isolated human NK cells in vitro (Dempsey, R. A., et al., J. Immunol. 129:2504 (1982); Phillips, J. H., et al. J. Exp. Med. 170:291 (1989)). Thus, the cytotoxic activity of NK cells treated with IL-2 is greater than the constitutive levels of cytotoxicity observed in untreated cells. Furthermore, depletion of NK-cells from animals eliminates IL-2's antitumor effects. (Mule, J. J. et al, J. Immunol. Invest. 139:285 (1987); Lotze, M. T. et al., supra). Additional evidence for the role of NK cells results from the observation that NK cells are the only resting human peripheral blood lymphocytes expressing the IL-2 receptor on their cell surface. (Caliguri, M. A. et al., J. Clin. Invst. 91:123–132 (1993).

Another cytokine with promise as an anti-cancer agent is interferon-$\alpha$. Interferon $\alpha$ (IFN-$\alpha$) has been employed to treat leukemia, myeloma, and renal cell carcinomas. Isolated NK cells exhibit enhanced cytotoxicity in the presence of IFN-$\alpha$. Thus, like IL-2, IFN-$\alpha$ also acts to augment NK cell mediated cytotoxicity. (Trinchieri, G. Adv. Immunol. 47:187–376 (1989)).

C. In Vivo Results of Histamine and Histamine Agonist Treatments

Histamine is a biogenic amine, i.e. an amino acid that possesses biological activity mediated by pharmacological receptors after decarboxylation. The role of histamine in immediate type hypersensitivity is well established. (Plaut, M. and Lichtenstein, L. M. 1982 Histamine and immune responses. In *Pharmacology of Histamine Receptors.*, Ganellin, C. R. and M. E. Parsons eds. John Wright & Sons, Bristol pp. 392–435.)

Examinations of whether histamine or histamine antagonists can be applied to the treatment of cancer have yielded contradictory results. Some reports suggest that administration of histamine alone suppressed tumor growth in hosts having a malignancy. (Burtin, Cancer Lett 12:195 (1981)). On the other hand, histamine has been reported to accelerate tumor growth in rodents (Nordlund, J. J. et al., J. Invest. Dermatol 81:28 (1983)).

Similarly, contradictory results were obtained when the effects of histamine receptor antagonists were evaluated. Some studies report that histamine receptor antagonists suppress tumor development in rodents and humans (Osband, M. E. et al., Lancet 1 (8221) :636 (1981). Other studies report that such treatment enhances tumor growth and may even induce tumors (Barna, B. P. et al., Oncology 40:43 (1983)).

D. Synergistic Effects of Histamine and IL-2

Despite the conflicting results when histamine is administered alone, recent reports clearly reveal that histamine acts synergistically with cytokines to augment the cytotoxicity of NK cells. Thus, therapies employing the combination of histamine and cytokines represent an attractive approach to anti-cancer strategies based on using the host immune system to attack the malignancy. Similarly, antiviral treatments using any of the well known antiviral agents is also contemplated.

Studies using histamine analogues suggest that histamine's synergistic effects are exerted through the $H_2$-receptors expressed on the cell surface of monocytes. For example, the $H_2$-receptor agonist dimaprit was capable of augmenting NK cell mediated cytotoxicity, while close structural analogues lacking biological activity failed to produce an effect. Additionally, $H_2$-receptor antagonists blocked the effects of histamine and dimaprit, implicating the $H_2$-receptor in the transduction of the histamine response. (Hellstrand, K. et al., J. Immunol. 137:656 (1986)).

Histamine's synergistic effect when combined with cytokines is not the result of a direct positive effect of histamine on NK cell cytotoxicity. Rather, the synergistic effects result from the suppression of a down regulation of NK cell cytotoxicity mediated by other cell types present along with the NK cells. The discussion below provides some of the evidence suggesting that histamine's synergistic effects result from the suppression of negative signals exerted by other cell types.

U.S. Pat. No. 5,348,739, which is incorporated herein by reference, discloses the synergistic effects of histamine and interleukin-2. As discussed above, IL-2 normally induces a cytotoxic response in NK cells. In vitro studies with NK cells alone confirm that cytotoxicity is stimulated when IL-2 is administered. However, in the presence of monocytes, the IL-2 induced enhancement of cytotoxicity of NK cells is suppressed.

In the absence of monocytes, histamine had no effect or weakly suppressed NK mediated cytotoxicity. (U.S. Pat. No. 5,348,739; Hellstrand, K. et al., J. Immunol. 137:656 (1986); Hellstrand, K. and Hermodsson, S., Int. Arch. Allergy Appl. Immunol. 92:379–389 (1990)). However, NK cells exposed to histamine and IL-2 in the presence of monocytes exhibit elevated levels of cytotoxicity relative to that obtained when NK cells are exposed only to IL-2 in the presence of monocytes. Id. Thus, the synergistic enhancement of NK cell cytotoxicity by combined histamine and interleukin-2 treatment results not from the direct action of histamine on NK cells but rather from suppression of an inhibitory signal generated by monocytes.

Without being limited to a particular mechanism, it is believed that the inhibitory effects of monocytes on NK mediated cytotoxicity result from the generation of $H_2O_2$ by monocytes. It has been reported that the production of $H_2O_2$ by monocytes suppresses NK cell cytotoxicity. (Van Kessel, K. P. M. et al., Immunology, 58:291–296 (1986); El-Hag, A. and Clark, R. A. J. Immuol. 133:3291–3297 (1984); Seaman, W. E. et al., J. Clin. Invest. 69:876–888 (1982)). Further evidence of the role of $H_2O_2$ in suppressing NK cell cytotoxicity comes from in vitro studies showing that the addition of catalase, an enzyme which acts to remove $H_2O_2$, to preparations of monocytes and NK cells exposed to IL-2 removes the inhibitory effects of the monocytes. (Seaman, supra.) Thus, histamine may exert its synergistic effects by reducing the level of $H_2O_2$ produced by monocytes. Hellstrand, K., Asea, A., Hermodsson, S. Histaminergic regulation of antibody-dependent cellular cytotoxicity of granulocytes, monocytes and natural killer cells, J. Leukoc. Biol. 55:392–397 (1994).

Monocytes are not the only cell type which negatively regulates NK cell cytotoxicity. Experiments have demonstrated that granulocytes suppress both the constitutive and IL-2 induced cytotoxic activity of NK cells in vitro. Like the monocyte mediated suppression discussed above, granulocyte mediated suppression is synergistically overcome by treatment with IL-2 and histamine. (U.S. Pat. No. 5,348,739; Hellstrand, K., Asea, A., Hermodsson, S. Histaminergic regulation of antibody-dependent cellular cytotoxicity of granulocytes, monocytes and natural killer cells, J. Leukoc. Biol. 55:392–397 (1994).

It appears that the $H_2$-receptor is involved in transducing histamine's synergistic effects on overcoming granulocyte mediated suppression. For example, the effect of histamine on granulocyte mediated suppression of antibody dependent cytotoxicity of NK cells was blocked by the $H_2$-receptor antagonist ranitidine and mimicked by the $H_2$ receptor agonist dimaprit. In contrast to the complete or nearly complete abrogation of monocyte mediated NK cell suppression by histamine and IL-2, such treatment only partially removed granulocyte mediated NK cell suppression. (U.S. Pat. No. 5,348,739; Hellstrand, K. et al., Histaminergic regulation of antibody dependent cellular cytotoxicity of granulocytes, monocytes and natural killer cells., J. Leukoc. Biol 55:392–397 (1994).

As suggested by the experiments above, therapies employing histamine and cytokines are effective anti-cancer strategies. U.S. Pat. No. 5,348,739 discloses that mice given histamine and IL-2 prior to inoculation with melanoma cell lines were protected against the development of lung metastatic foci. This effect was a consequence of synergistic interaction between histamine and IL-2, as demonstrated by the significant reduction in metastatic foci observed in mice given histamine and IL-2 as compared to mice given histamine or IL-2 alone.

In addition to the synergistic effects observed in the assay of lung metastatic foci, synergistic effects of histamine plus IL-2 treatment were also observed in assays in which NK cell cytotoxicity was measured by determining the ability of mice to kill malignant cell lines derived from both humans and mice which were injected into them. Id.

The above results demonstrate that strategies employing a combination of histamine and IL-2 are an effective means of treating malignancies.

E. Synergistic Effects of Histamine and Interferon-α

Histamine also acts synergistically with interferon-α to overcome the suppression of NK cell cytotoxicity by monocytes (Hellstrand et al., Regulation of the NK cell response to interferon-alpha by biogenic amines, J. Interferon Res. 12:199–206 (1992)). Like IL-2, interferon-α augments NK cell constitutive NK cell cytotoxicity. Id. Monocytes suppress the interferon-α mediated enhancement of NK cell killing of malignant target cells in vitro. Monocyte mediated suppression of NK cell cytotoxicity was overcome by treatment with histamine and interferon-α. The effects of histamine were blocked by $H_2$-receptor antagonists and mimicked by $H_2$-receptor agonists. Compounds bearing structural similarity to the $H_2$-receptor agonist dimaprit but lacking the activity of the agonist were unable to act synergistically with interferon-α. (Hellstrand et al. J., Interferon Res. 12:199–206 (1992)).

F. Human Treatments Combining Histamine, Interleukin-2 and Interferon-α

The in vitro and animal results discussed above suggested that histamine+IL-2+interferon-α was a promising method for treating human malignancies. In fact, combined histamine, IL-2, and interferon-α treatments have proven effective in the treatment of a variety of human malignancies, providing a 75% response rate significantly greater than that observed with IL-2 alone. (Hellstrand et al., Histamine in Immunotherapy of Advanced Melanoma: A Pilot Study, Cancer Immunology and Immunotherapy 39: 416–419 (1994). In the above study, subjects received a constant infusion of IL-2 (Proleukin®, Eurocetus), $18 \times 10^6$ U/m$^2$ on days 1–5 and 8–12, repeated every 4–6 weeks, as well as interferon-α ($6 \times 10^6$ U daily, s.c.). In addition to the IL-2, eight of the subjects received histamine dihydrochloride (1 mg s.c.) twice daily. Id.

Only one subject in the group receiving IL-2 and interferon-α exhibited a partial or mixed response, a response rate of 14% (1 of 7). In contrast, the group receiving both IL-2, interferon-α and histamine showed an corresponding response rate of 75% (6 of 8). Only two of these subjects failed to respond. Id.

Thus, histamine+IL-2+interferon-α is an effective anti-cancer therapy.

G. Human Treatments with Histamine+IL-2+ Chemotherapeutic Agents

Recently, the efficacy of treatments employing histamine, IL-2, and chemotherapeutic agents was examined in humans suffering from acute myelogenous leukemia (AML) (Brune and Hellstrand, Remission Maintenance Therapy with Histamine and Interleukin-2 in Acute Myelogenous Leukemia, Br. J. Haematology, March 1996).

In one set of experiments, killing of AML blasts by NK cells was examined in vitro. IL-2 induced NK mediated cytotoxicity, but this effect was suppressed by monocytes. Histamine did not affect the IL-2 induced cytotoxic response in the absence of monocytes but blocked the suppressive effects of the monocytes. However, in the presence of the H$_2$-receptor antagonist ranitidine, histamine was ineffective in overcoming the monocyte suppression. Id.

Additionally, AML patients in remission were treated with histamine+IL-2+the chemotherapeutic agents cytarabine and thioguanine and the duration of remission was measured and compared to the length of remissions prior to initiating the treatment. Five of the patients receiving histamine+IL-2+cytarabine+ thioguanine remained in complete remission ranging in duration from 9–27 months at the time of publication. Two patients relapsed after remissions lasting 8 and 33 months. In the five patients who had undergone a remission followed by a relapse prior to initiation of the histamine+IL-2+cytarabine+ thioguanine regimen, the duration of remissions following initiation of the regimen exceeded the duration of the prior remission. Id. Such "inversion of remission time" is rare in the natural course of AML and reportedly only occurs in a small fraction (<10%) of AML patients treated with IL-2 as the single agent. Shepherd et al, Phase II Study of Subcutaneous rHU IL-2 in Patients with Acute Myelogenous Leukemia in Partial or Complete Second Remission and Partial Relapse, Br. J. Haematol. S87, 205 (1994).

Thus, histamine+IL-2+chemotherapeutic agents is an effective anti-cancer therapy.

SUMMARY OF THE INVENTION

The present invention relates to treatments combining the administration of histamine to achieve a beneficial level of circulating blood histamine with treatment with a second agent which enhances natural killer cell cytotoxicity. Alternatively, the invention relates to treatments which combine the administration of histamine to achieve beneficial levels of circulating blood histamine with treatment with a chemotherapeutic agent. Combinations of histamine, agents which enhance NK cell cytotoxicity, and chemotherapeutic agents are also contemplated. It will be appreciated that the beneficial stable levels of circulating blood histamine may be attained by administering histamine before, during, after or throughout the course of the administration of the second agent. As used herein "stable" means a level that is maintained for hours or preferably, days.

Thus the present invention includes a method of augmenting the activity of an agent which enhances natural killer cell cytotoxicity comprising:

a) administering a pharmaceutically acceptable form of histamine such that a stable blood histamine concentration sufficient to augment the cytotoxicity enhancing effect of said agent is achieved; and b) administering a beneficial amount of said agent, wherein the cytotoxicity enhancing effects of said agent are augmented.

This invention also relates to a method of treating a subject having a malignancy with histamine and a second beneficial agent wherein the activity of said second beneficial agent is augmented by histamine comprising:

a) administering a pharmaceutically acceptable form of histamine such that a beneficial blood histamine level is achieved; and b) administering said second beneficial agent.

The invention also comprises a method of enhancing the cytotoxic activity of natural killer cells comprising:

a) measuring blood histamine levels in a subject to determine whether the cytotoxic activity of said subject's natural killer cells could be enhanced by increasing the levels of blood histamine in said subject;

b) administering a pharmaceutically acceptable form of histamine to a subject for whom said measuring step indicated that the cytotoxic activity of said subject's natural killer cells could be enhanced by increasing said subject's blood histamine levels, such that beneficial levels of blood histamine are achieved; and c) administering a second agent to said subject having beneficial levels of blood histamine, such that the cytotoxic activity of said subject's natural killer cells is enhanced.

Another aspect of the invention is method of treating a malignancy comprising treating a subject having a malignancy with a chemotherapeutic agent and maintaining a beneficial stable level of circulating blood histamine by administering a pharmaceutically acceptable form of histamine in a dose sufficient to attain said beneficial stable levels of circulating blood histamine.

A more complete appreciation of the invention and many of the attendant advantages thereof will be readily perceived as the same becomes better understood by reference to the following detailed description when considered in connection with the accompanying figures.

Other objects, advantages and features of the present invention will become apparent to those skilled in the art from the following discussion.

DETAILED DESCRIPTION OF THE PREFERRED EMBODIMENTS

Figure 1:
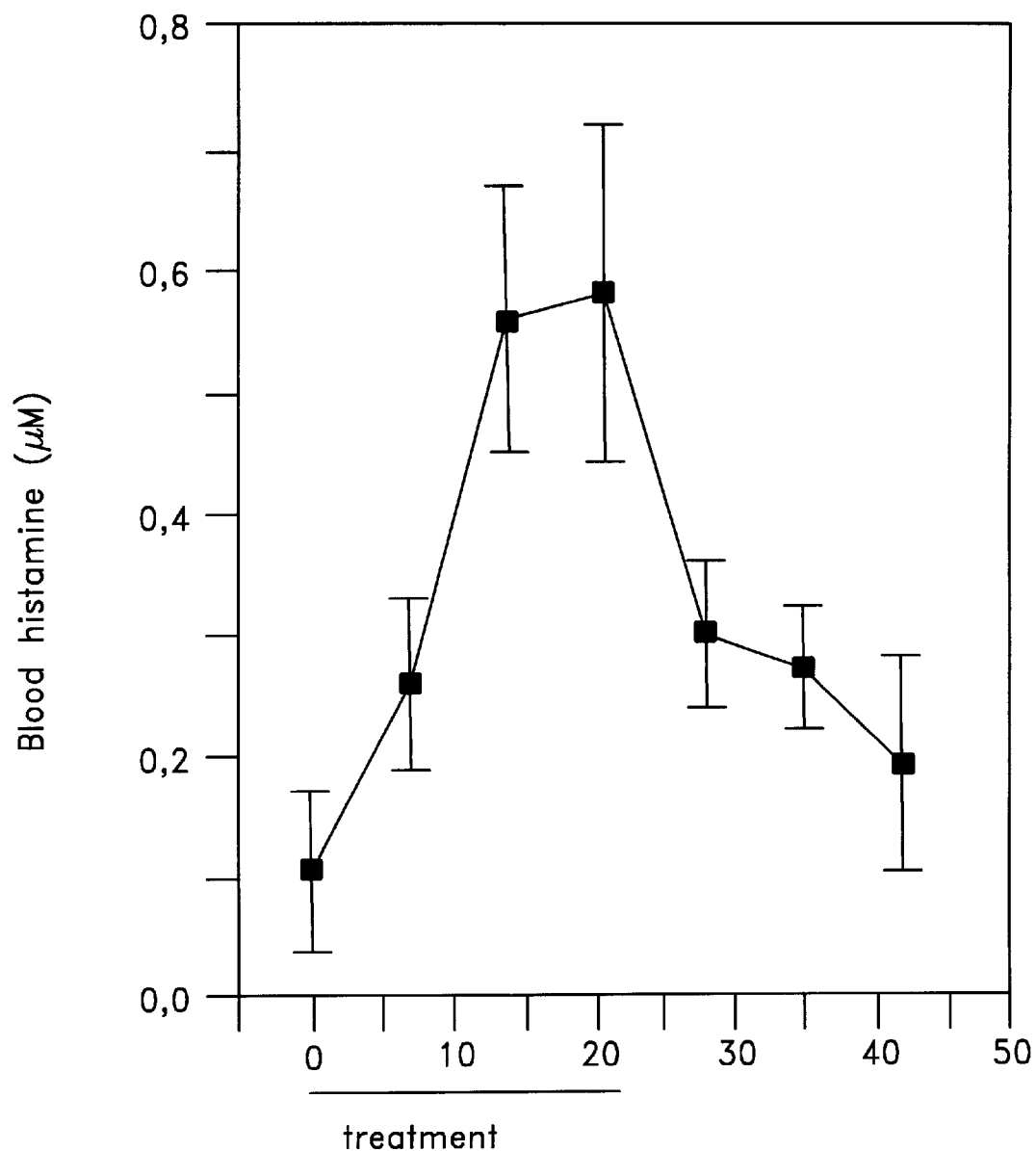
FIG. 1 shows that it is possible to obtain stable beneficial levels of circulating blood histamine.

Prior to the present invention, histamine was believed to have an extremely short half life, on the order of five minutes, in the blood. Beaven, M. A., Factors regulating availability of histamine at tissue receptors in Pharmacology of Histamine Receptors, C. R. Ganellin and M. E. Parsons eds., Wright PSG, Bristol, U.K. pp. 103–145 (1982). The present invention arose from the unexpected finding that, contrary to the prior reports, it is possible to achieve stable levels of circulating blood histamine lasting several hours or even days from the time of histamine administration. The present invention is the first report of stable circulating blood histamine. Using regimens involving the administration of both $H_2$-receptor antagonists and histamine, Burtin was able to obtain normal levels of circulating blood histamine in cancer subjects experiencing stabilization of the disease. (Burtin et al., Eur. J. Clin. Oncol. 24: 161–167 (1988)). However, the normal levels reported by Burtin were most likely a consequence of the stabilization of the cancer rather than an observation of stable circulating levels of histamine for a significant period following administration. Evidence that the levels reported in Burtin were a consequence of physiological stabilization comes from the fact that the normal levels of histamine reported by Burtin when the subjects experienced a remission dropped to below normal levels before the subjects' deaths. Burtin did not specify the time after administration at which circulating histamine levels were measured, but it seems likely that the normal levels reported by Burtin were a consequence of endogenously produced histamine associated with stabilization of the cancer rather than an observation of persistence of extrinsically administered histamine.

Subjects suffering from cancer often exhibit decreased levels of circulating blood histamine. (Burtin et al. Decreased blood histamine levels in subjects with solid malignant tumors, Br. J. Cancer 47: 367–372 (1983). Thus, the observation of stable and beneficial blood histamine levels lasting hours or days after histamine administration finds ready application to cancer treatments based on synergistic effects between histamine and agents which enhance NK cell mediated cytotoxicity. In such protocols, the cytotoxic activity of NK cells is enhanced by combining the administration of histamine to attain a stable level of circulating histamine sufficient to augment the activity of an agent which acts in synergy with histamine to increase NK mediated cytotoxicity with the administration of the agent.

Additionally, chemotherapeutic treatments aimed at destroying the malignancy may result in lowered blood histamine levels. Example 1, below describes the decrease in blood histamine levels following treatment with the chemotherapeutic/cytostatic agents cytarabine and thioguanine.

EXAMPLE 1

In five patients with AML in remission, histamine levels in whole blood specimens were analyzed 1–5 days before and 1–2 weeks after treatment with cytarabine (16 mg/m$^2$/day subcutaneously) and thioguanine (40 mg/day orally) for 21 days or until the platelet count was $\leq 50 \times 10^9$/l. Histamine was analyzed in heparinized venous blood using the radioimmunoassay available from Biomerica Inc., Newport Beach, Calif. 92663 (catalog no. 1051) according to the instructions which accompanied the assay kit.

In all patients, histamine levels declined after the treatment with cytostatics. (See Table below).

| Blood Histamine Before Patient Treatment ($\mu$moles/l) | Blood Histamine after Treatment ($\mu$moles/l) |
|---|---|
| 1. 0.22 | not detectable |
| 2. 0.12 | not detectable |
| 3. 0.18 | not detectable |
| 4. 0.93 | 0.38 |
| 5. 0.24 | 0.14 |

The present invention may be used to restore or maintain beneficial stable blood histamine levels in subjects whose blood histamine levels have decreased as a consequence of chemotherapy.

Beneficial levels of circulating histamine can be achieved by administering histamine before, during, or after treatment with agents which enhance natural killer cell cytotoxicity or chemotherapeutic agents.

Thus, this invention relates to a method of augmenting the activity of an agent which enhances natural killer cell cytotoxicity comprising administering histamine such that a stable blood histamine concentration sufficient to augment the cytotoxicity enhancing effect of said agent is achieved, and administering a beneficial amount of said agent, wherein the cytotoxicity enhancing effects of said agent are augmented.

In one aspect of the present invention, the histamine is administered prior to the agent which enhances natural killer cell cytotoxicity. In another embodiment, the histamine is administered following the administration of the agent which enhances natural killer cell cytotoxicity. In a further embodiment, the histamine is administered during the course of administration of the agent which enhances natural killer cell cytotoxicity. In another embodiment, the histamine is administered prior, during, and after the administration of the agent which enhances natural killer cell cytotoxicity.

In one embodiment, the histamine is administered at least 1 day prior to the administration of the agent which enhances natural killer cell cytotoxicity. In a preferred embodiment beneficial stable levels of circulating blood histamine are obtained by administering histamine at a dosage of 0.4 to 10 mg/day. In a further preferred embodiment, the histamine is administered over a period of 1 to 4 weeks. In a highly preferred embodiment, the histamine is administered for a period of 1–2 weeks. In one embodiment of the invention, the beneficial stable level of circulating blood histamine concentration is at least 0.2 $\mu$mol/L.

In one embodiment of the present invention the NK cell cytotoxicity enhancing agent is at least one cytokine. Preferentially, the cytokine is interleukin-2. In a preferred aspect of the invention, the interleukin-2 is administered in an amount of 0.5–50 $\mu$g/kg/day. In a further preferred embodiment, the interleukin-2 is administered for a period of 1 day to 4 weeks.

In another embodiment of the invention, the cytokine is interferon-$\alpha$. Preferentially, the interferon-$\alpha$ is administered at a dosage of 10,000–200,000 U/kg/day. For treatment of primary melanoma, the preferred dosage of interferon-$\alpha$ is 200,000 U/kg/day. For treatment of other cancers, the preferred dosage of interferon-$\alpha$ is 50,000 U/kg/day. In a further embodiment, the interferon-$\alpha$ is administered for a period of up to 18 months. Preferentially, the interferon-$\alpha$ is administered for a period of between 2–6 weeks.

In yet another embodiment, the natural killer cell cytotoxicity enhancing agent comprises interferon-$\alpha$ and interleukin-2.

Another aspect of the invention is a method of treating a subject having a malignancy with histamine and a second beneficial agent wherein the activity of said second beneficial agent is augmented by histamine comprising administering a pharmaceutically acceptable form of histamine such that a beneficial blood histamine level is achieved and administering said second beneficial agent.

In one embodiment of this aspect, the histamine is administered prior to the second beneficial agent. In a preferred embodiment of this aspect, the histamine is administered at least 1 day prior to the administration of the second beneficial agent.

In another embodiment of this invention, the histamine is administered after the second beneficial agent. In yet another embodiment, the histamine is administered during the course of administration of said second beneficial agent. In another aspect of the invention, the histamine is administered prior, during, and after the second beneficial agent.

Preferentially, the second beneficial agent acts to stimulate the cytotoxic activity of natural killer cells.

A third aspect of the present invention is a method of enhancing the cytotoxic activity of natural killer cells comprising a) measuring blood histamine levels in a subject to determine whether the cytotoxic activity of said subject's natural killer cells could be enhanced by increasing the levels of blood histamine in said subject.

b) administering a pharmaceutically acceptable form of histamine to a subject for whom said measuring step indicated that the cytotoxic activity of said subject's natural killer cells could be enhanced by increasing said subject's blood histamine levels, such that beneficial levels of blood histamine are achieved. and c) administering a second agent to said subject having beneficial levels of blood histamine, such that the cytotoxic activity of said subject's natural killer cells is enhanced.

In one aspect of the invention, the histamine is administered prior to the second agent. In a preferred version of this aspect, the histamine is administered at least 1 day prior to the administration of the second agent.

In another aspect of the invention, histamine is administered after the second agent. In another embodiment, histamine is administered during the administration of the second agent. In another embodiment, the histamine is administered prior, during, and after the administration of the second agent. In each instance, one embodiment of the invention includes an antiviral or antimicrobial agent as the second agent.

The present invention also includes a method of treating a malignancy comprising treating a subject having a malignancy with a chemotherapeutic agent and achieving and maintaining a beneficial stable level of circulating blood histamine by administering histamine in a dose sufficient to attain said beneficial stable levels of circulating blood histamine.

In one embodiment, the histamine is administered before the chemotherapeutic agent. In another embodiment, the histamine is administered after the chemotherapeutic agent. In another aspect of the invention, the histamine is administered during treatment with the chemotherapeutic agent. In yet another embodiment, the histamine is administered prior, during, and after treatment with the chemotherapeutic agent.

It will be appreciated that the subject's circulating blood histamine levels may be monitored during the course of treatment and boosted to beneficial levels whenever levels drop below beneficial levels or approach the lower limits of beneficial levels. For example, in this embodiment, histamine may be administered whenever the subject's histamine levels drop below 0.2 $\mu$mole/L.

Alternatively, it will be appreciated that histamine may be administered at periodic intervals at dosages sufficient to establish and maintain beneficial levels.

Routes and carrier compositions for administering histamine and cytokines have been disclosed in U.S. Pat. No. 5,348,739, which is incorporated herein by reference. Additionally, methods for administering chemotherapeutic agents are well established.

For the purposes of the above treatments, beneficial levels of blood histamine are at least 0.2 $\mu$mole/L.

Stable Circulating Blood Histamine Levels

As described above, the present invention is based on the observation that it is possible to obtain beneficial and stable levels of circulating blood histamine. Example 2 depicts the stable beneficial levels of circulating blood histamine obtained following histamine administration. Surprisingly, beneficial levels of circulating blood histamine persisted for considerable periods after histamine administration ceased.

EXAMPLE 2

Five patients with AML in remission received treatment with histamine dihydrochloride diluted in sterile sodium chloride purchased from Apoteksbolaget, Umea, Sweden and human recombinant interleukin-2 (Proleukin®) obtained from the commercially available vial (Eurocetus, the Netherlands) Histamine and IL-2 were administered morning and night at separate subcutaneous injection sites over a period of 21 consecutive days. The histamine was given as subcutaneous injections using 1 ml syringes containing 0.1 mg of histamine/ml. The histamine treatment was given twice daily (morning and night) at a dosage of 0.4–0.7 mg histamine per injection (i.e. a daily total dose of histamine of 0.8–1.4 mg/day).

The IL-2 was given as subcutaneous injections using separate 1-ml syringes. The IL-2 syringes contained 50 $\mu$g of IL-2/ml. The IL-2 treatment was given twice daily (morning and night), and the dose was 35–50 $\mu$g of IL-2 per injection, i.e. a daily total dose of 70–100 $\mu$g/day.

Peripheral blood venous samples were drawn in 10 ml heparinized test tubes before the onset of treatment and weekly thereafter. The samples were drawn at least 8 hours after the last injections of histamine and IL-2. The concentration of histamine in the whole blood samples was analyzed by use of a double antibody radioimmunoassay kit obtained from Biomerica, Inc., Newport Beach, Calif. 92663 (catalog no. 1051). The manufacturer's instructions provided with the kit, dated June, 1989, were followed. Blood histamine levels were measured at the indicated times.

FIG. 1 shows the results of the experiments described above. Data are given as the concentration of histamine in micromoles/1 (mean±standard error of the mean).

The subjects exhibited blood histamine levels of less than 0.2 $\mu$mole/L at the start of the experiment. Following histamine administration, circulating blood histamine levels rose to beneficial levels. Surprisingly, the circulating blood histamine levels remained elevated for sustained periods of time, even after histamine administration was discontinued.

Treatments Employing a Combination of Histamine and Interleukin-2

The stable blood histamine levels discussed above find application in treatments in which natural killer cell cytotoxicity is augmented through the synergistic effects of histamine and agents which enhance NK cell cytotoxicity. As discussed above, one such enhancer of NK cytotoxicity is interleukin-2. Example 3 describes methods of treatment in which a stable and beneficial level of histamine is achieved which augments the activity of IL-2.

EXAMPLE 3

0.5 mg/day of histamine in a pharmaceutically acceptable form is injected subcutaneously in a sterile carrier solution into subjects having a malignancy. One week later, after circulating blood histamine levels have increased to at least 0.2 $\mu$mole/L, IL-2 administration is begun. Human recombinant IL-2 (Proleukin®, Eurocetus) is administered by continuous infusion of 27 $\mu$g/kg/day on days 1–5 and 8–12.

The above procedure is repeated every 4–6 weeks until an objective regression of tumor disease is observed. The therapy may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 $\mu$mole/L, injecting 0.5 mg/day of a pharmaceutically acceptable form of histamine to restore circulating blood histamine levels above 0.2 $\mu$mole/L .

The treatment can also include periodically boosting circulating blood histamine levels by administering 0.5 mg/day histamine over a period of one to two weeks at regular intervals, such as bi-weekly, in order to maintain circulating blood histamine levels above 0.2 $\mu$mole/L.

Combination of Histamine and Interferon-$\alpha$

Another enhancer of NK cell cytotoxicity is interferon-$\alpha$. Example 4 describes methods of treatment in which a stable and beneficial level of histamine is achieved which augments the activity of interferon-$\alpha$.

EXAMPLE 4

0.5 mg/day of histamine in a pharmaceutically acceptable form is injected subcutaneously in a sterile carrier solution into subjects having a malignancy or who have had a primary tumor surgically removed. One week later, after circulating blood histamine levels have increased to at least 0.2 $\mu$mole/L, interferon-$\alpha$ administration is begun. Interferon is administered in doses of 50,000 U/kg/day in a suitable carrier solution for 2–6 weeks.

The above procedure is repeated at intervals of sometimes for 18 months or 3 times a week for 18 months until an objective regression of the tumor is observed. The therapy with histamine, IL-2 and interferon may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 $\mu$mole/L, injecting 0.5 mg/day of a pharmaceutically acceptable form of histamine to restore circulating blood histamine levels above 0.2 $\mu$mole/L.

The treatment can also include periodically boosting circulating blood histamine levels by administering 0.5 mg/day histamine over a period of one to two weeks at regular intervals, such as bi-weekly, in order to maintain circulating blood histamine levels above 0.2 $\mu$mole/L.

Additionally, the frequency of interferon-$\alpha$ administration may be varied depending on the patient's tolerance of the treatment and the success of the treatment. For example, interferon may be administered three times per week, or even daily, for a period of up to 18 months. Those skilled in the art are familiar varying interferon treatments to achieve both beneficial results and patient comfort.

Combination of Histamine, IL-2 and Interferon-$\alpha$

Beneficial stable levels of circulating blood histamine can also be employed in conjunction with treatments involving several enhancers of NK cell cytotoxicity. Example 5 describes how to administer such treatments.

EXAMPLE 5

0.5 mg/day of histamine in a pharmaceutically acceptable form is injected subcutaneously into subjects having a malignancy in a sterile carrier solution. One week later, after circulating blood histamine levels have increased to at least 0.2 $\mu$mole/L, human recombinant IL-2 (Proleukin®, Eurocetus) is administered by continuous infusion of 27 $\mu$g/kg/day on days 1–5 and 8–12. Additionally, subjects also receive a daily dose of 6×10$^6$ U interferon-$\alpha$ administered by subcutaneous injection.

The above procedure is repeated every 4–6 weeks until an objective regression of the tumor is observed. The therapy may be continued even after a partial or complete response has been observed. In patients with complete responses, the therapy may be given with longer intervals between cycles.

The treatment can additionally include monitoring circulating levels of blood histamine periodically and, when circulating histamine levels drop below 0.2 $\mu$mole/L, injecting 0.5 mg/day of a pharmaceutically acceptable form of histamine for a period of one to two weeks to restore circulating blood histamine levels above 0.2 $\mu$mole/L .

The treatment can also include periodically boosting circulating blood histamine levels by administering histamine at regular intervals, such bi-weekly.

Additionally, the frequency of interferon-$\alpha$ administration may be varied depending on the patient's tolerance of the treatment and the success of the treatment. For example, interferon may be administered three times per week, or even daily, for a period of up to 18 months. Those skilled in the art are familiar varying interferon treatments to achieve both beneficial results and patient comfort.

Combination of Histamine and Chemotherapeutic Agents

Histamine may also be used in conjunction with chemotherapeutic agents. Typically, levels of circulating histamine decline during chemotherapy. Low levels of circulating histamine may result in the suppression of NK cell cytotoxicity by monocytes. This monocyte mediated suppression may be eliminated by administration of histamine prior, during, following or throughout chemotherapy in order to return circulating histamine levels to normal.

Accordingly, the present invention contemplates the restoration of circulating blood histamine levels to normal levels in conjunction with chemotherapeutic agents. Additionally, the treatment may also include administration of IL-2 and/ or interferon-$\alpha$.

Representative compounds used in cancer therapy include cyclophosphamide, choroambucil, melphalan, estramustine, iphosphamide, prednimustin, busulphan, tiottepa, carmustin, lomustine, methotrexate, azathioprine, mercaptopurine, thioguanine, cytarabine, fluorouracil, vinblastine, vincristine, vindesine, etoposide, teniposide, dactinomucin, doxorubin, dunorubicine, epirubicine, bleomycin, nitomycin, cisplatin, carboplatin, procarbazine, amsacrine, mitoxantron, tamoxifen, nilutamid, and aminoglutemide. Procedures for employing these compounds against malignancies are well established. In addition, other cancer therapy compounds may also be utilized in the present invention.

Malignancies against which the treatment may be directed include, but are not limited to, primary and metastatic malignant tumor disease, hematological malignancies such as acute and chronic myelogenous leukemia, acute and chronic lymphatic leukemia, multiple myeloma, Waldenstroms Macroglobulinemia, hairy cell leukemia, myelodysplastic syndrome, polycytaemia vera, and essential thrombocytosis.

As described above, histamine+IL-2 has proven an effective combination with traditional chemotherapeutic methods in treating acute myelogenous leukemia. (Brune and Hellstrand, Br. J. Haematology, March 1996). Procedures for using the present invention in combination with chemotherapeutic agents and IL-2 are presented in Example 6. It will be appreciated that beneficial stable levels of circulating histamine may also be employed in treatments using only chemotherapeutic agents.

EXAMPLE 6

Subjects with AML in first, second, subsequent or complete remission are treated in 21-day courses with IL-2 [35–50 $\mu$g (equivalent to 6.3–9×$10^5$ IU) s.c. twice daily], repeated with six-week intermissions and continued until relapse. In cycle #1, patients receive three weeks of low dose chemotherapy consisting of 16 mg/m2/day cytarabine, and 40 mg/day thioguanine. Thereafter, patients are injected subcutaneously with 0.5 mg/day of a pharmaceutically acceptable form of histamine for a period of 1 week to boost circulating histamine to a stable beneficial level above 0.2 $\mu$mole/L. Thereafter, patients receive 100 $\mu$g of interleukin-2/day for three weeks. Circulating histamine levels are boosted to beneficial levels by administering 0.5 mg/day of a pharmaceutically acceptable form of histamine during the second week of this period. Thereafter, the subjects are allowed to rest for one week.

After the rest period at the end of cycle 1, cycle #2 is initiated. 0.5 mg/day of a pharmaceutically acceptable form of histamine in a sterile carrier solution is injected subcutaneously until circulating blood histamine levels of at least 0.2 $\mu$mole/L are achieved. Cytarabine (16 mg/m$^2$/day s.c.) and thioguanine (40 mg/day orally) are given for 21 days (or until the platelet count is $\leq$50×$10^9$/1). In the middle week, patients receive 0.5 mg/day of a pharmaceutically acceptable form of histamine to boost circulating histamine to beneficial levels. At the end of the three week chemotherapy treatment, patients receive 0.5 mg/day of a pharmaceutically acceptable form of histamine for a week. Thereafter, patients receive 100 $\mu$g/day of interleukin-2 for three weeks. Circulating histamine levels are boosted in the middle week of the three week IL-2 treatment as described above. Patients are permitted to rest for two weeks.

Thereafter, cycle #3 is initiated. Cycle #3 is identical to cycle #2.

Alternatively, circulating histamine levels may be periodically monitored throughout the above procedure and histamine may be administered whenever circulating levels drop below a desirable level in order to maintain a beneficial level of blood histamine above 0.2 $\mu$mole/L. Additionally, histamine may be administered at regular intervals during the treatment to maintain beneficial circulating levels. Another alternative is to provide histamine in a depot or controlled release form. Numerous controlled release vehicles are known, including biodegradable or bioerodable polymers such as polylactic acid, polyglycolic acid, and regenerated collagen. Implantble or injectalbe polymer matrices from which active ingredients are slowly released are also well known. Finally, transdermal patches or formulations, with or without, use of a penetration enhancer such as DMSO or Azone can be used in the present invention.

What is claimed is:

1. A method of augmenting the activity of an agent which enhances natural killer cell cytotoxicity comprising:
    a) administering a plurality of doses of histamine in a pharmaceutically acceptable form over a period of at least 1 week prior to administration of said agent such that a stable, circulating blood histamine concentration sufficient to augment the cytotoxicity enhancing effect of said agent is achieved; and
    b) administering a beneficial amount of said agent after said stable, circulating blood histamine concentration is achieved, wherein the cytotoxicity enhancing effects of said agent are augmented.

2. The method of claim 1 further comprising administering histamine prior to, during the course of and after administration of said agent which enhances natural killer cell cytotoxicity.

3. The method of claim 1 wherein said agent is at least one cytokine.

4. The method of claim 1 wherein said stable blood histamine concentration is at least 0.2 $\mu$mole/L.

5. The method of claim 3 wherein the cytokine is interleukin-2.

6. The method of claim 5 wherein the interleukin-2 is administered in the dosage of 0.5–50 $\mu$g/kg/day.

7. The method of claim 6 wherein the interleukin-2 is administered for a period of 1 day to 4 weeks.

8. The method of claim 3 wherein the cytokine is interferon-$\alpha$.

9. The method of claim 8 wherein the interferon-$\alpha$ is administered over a period of 2–6 weeks.

10. The method of claim 8 wherein the interferon-$\alpha$ is administered in the dosage of 10,000–200,000 U/kg/day.

11. The method of claim 8 wherein the interferon-$\alpha$ is administered in the dosage of 50,000 U/kg/day.

12. The method of claim 1 wherein the histamine is administered in a dose of 0.4 to 10 mg/day.

13. The method of claim 12 wherein the histamine is administered over a period of 1 to 4 weeks.

14. The method of claim 12 wherein the histamine is administered over a period of 1 to 2 weeks.

15. The method of claim 1 wherein said agent comprises interferon-$\alpha$ and interleukin-2.

16. A method of treating a subject having a malignancy with histamine and a second beneficial agent wherein the activity of said second beneficial agent is augmented by histamine comprising:
    a) administering a plurality of doses of histamine in a pharmaceutically acceptable form at least 1 week prior to administration of said second beneficial agent such that a stable, circulating beneficial blood histamine level is achieved; and
    b) administering said second beneficial agent after said stable beneficial histamine level is achieved.

17. The method of claim 16 wherein histamine is further administered during the course of administration of said second beneficial agent.

18. The method of claim 16 wherein histamine is administered prior, during, and after administration of said second beneficial agent.

19. The method of claim 16 wherein the second beneficial agent acts to stimulate the cytotoxic activity of natural killer cells.

20. A method of enhancing the cytotoxic activity of natural killer cells comprising:
   a) measuring blood histamine levels in a subject to determine whether the cytotoxic activity of said subject's natural killer cells could be enhanced by increasing the levels of blood histamine in said subject;
   b) administering a plurality of doses of histamine in a pharmaceutically acceptable form to a subject for whom said measuring step indicated that the cytotoxic activity of said subject's natural killer cells could be enhanced by increasing said subject's blood histamine levels, such that stable beneficial levels of circulating blood histamine are achieved; and
   c) administering a second agent to said subject having beneficial levels of blood histamine, such that the cytotoxic activity of said subject's natural killer cells is enhanced, wherein said second agent is administered at least one week subsequent to administration of said plurality of doses of histamine.

21. The method of claim 20 wherein histamine is further administered during the administration of said second agent.

22. The method of claim 20 wherein histamine is administered prior, during, and after the administration of said second agent.

23. A method of treating a malignancy comprising:
   a) providing a beneficial stable level of circulating blood histamine in a subject having a malignancy at least one week prior to subsequent chemotherapy by administering a plurality of doses of histamine in a pharmaceutically acceptable form sufficient to attain said beneficial stable level of circulating blood histamine; and
   b) treating the subject having a malignancy with a chemotherapeutic agent after said beneficial stable level of circulating blood histamine is attained.

24. The method of claim 23 wherein histamine is further administered during treatment with the chemotherapeutic agent.

25. The method of claim 23 wherein histamine is administered prior, during, and following treatment with the chemotherapeutic agent.

26. A method of treating a subject having a malignancy, comprising:
   administering to said subject a plurality of doses of histamine in a pharmaceutically acceptable form;
   determining when a stable circulating histamine level has been achieved in the subject; and
   administering to the subject, in response to achievement of stable circulating histamine level, an agent that stimulates the cytotoxicity of natural killer cells at least one week subsequent to achieving said stable circulating histamine level.

27. The method of claim 26, wherein said agent is a cytokine.

28. The method of claim 27, wherein said cytokine is IL-2.

29. The method of claim 12, wherein the histamine is administered twice daily.

30. The method of claim 16, wherein the histamine is administered twice daily.

31. The method of claim 16, wherein the histamine is administered for a period of 1 to 4 weeks.

32. The method of claim 20, wherein the histamine is administered twice daily.

33. The method of claim 20, wherein the histamine is administered for a period of 1 to 4 weeks.

34. The method of claim 23, wherein the histamine is administered twice daily.

35. The method of claim 23, wherein the histamine is administered for a period of 1 to 4 weeks.

36. The method of claim 26, wherein the histamine is administered twice daily.

37. The method of claim 26, wherein the histamine is administered for a period of 1 to 4 weeks.

* * * * *